(12) United States Patent
Lok et al.

(10) Patent No.: US 9,448,197 B2
(45) Date of Patent: *Sep. 20, 2016

(54) MARKER FOR READINGS TAKEN FROM ALTERNATIVE SITE TESTS

(71) Applicant: Ascensia Diabetes Care Holdings AG, Basel (CH)

(72) Inventors: Hoi-Wah Derek Lok, Mohegan Lake, NY (US); Robert Trzybinski, Granger, IN (US); Mohammad A. Kheiri, Plainfield, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 30 days.

This patent is subject to a terminal disclaimer.

(21) Appl. No.: 13/826,105

(22) Filed: Mar. 14, 2013

(65) Prior Publication Data

US 2013/0196421 A1    Aug. 1, 2013

Related U.S. Application Data

(63) Continuation of application No. 11/792,322, filed as application No. PCT/US2005/044802 on Dec. 12, 2005, now Pat. No. 8,444,575.

(60) Provisional application No. 60/635,574, filed on Dec. 13, 2004.

(51) Int. Cl.
*A61B 5/00* (2006.01)
*G01N 27/26* (2006.01)
(Continued)

(52) U.S. Cl.
CPC ............ *G01N 27/26* (2013.01); *A61B 5/1411* (2013.01); *A61B 5/1486* (2013.01);
(Continued)

(58) Field of Classification Search
CPC .......... A61B 5/1411; A61B 5/150175; A61B 5/150183; G01N 27/26; G01N 33/48792
USPC ........................ 600/573, 583, 584; 606/181
See application file for complete search history.

(56) References Cited

U.S. PATENT DOCUMENTS

| 7,238,160 B2 | 7/2007 | Taniike et al. |
| 2002/0082521 A1 | 6/2002 | Sharma et al. |

(Continued)

FOREIGN PATENT DOCUMENTS

| EP | 1464282 | 10/2004 |
| WO | 03/045233 | 6/2003 |
| WO | 2004/064635 | 8/2004 |

OTHER PUBLICATIONS

Fineberg, S. E. et al. "Use of an Automated Device for Alternative Site Blood Glucose Monitoring." Diabetes Care. vol. 24, No. 7, Jul. 2001 (pp. 1217-1220).

(Continued)

*Primary Examiner* — Linda Dvorak
*Assistant Examiner* — Emily Lloyd
(74) *Attorney, Agent, or Firm* — Nixon Peabody LLP

(57) ABSTRACT

A meter for determining the concentration of an analyte in a fluid sample comprises a memory device, electrical circuitry and a detection device for distinguishing between an alternative site test and a standard site test. The memory device is adapted to store information. The electrical circuitry is adapted to determine the analyte concentration of the fluid sample located on a test sensor. The electrical circuitry is in electronic communication with the memory device. The electrical circuitry communicates the determined analyte concentration to the memory device for storage.

20 Claims, 4 Drawing Sheets

(51) Int. Cl.
| | |
|---|---|
| *A61B 5/15* | (2006.01) |
| *A61B 5/1486* | (2006.01) |
| *G01N 33/487* | (2006.01) |
| *A61B 5/151* | (2006.01) |
| *A61B 5/157* | (2006.01) |
| *A61B 5/145* | (2006.01) |

(52) U.S. Cl.
CPC .......... *A61B 5/14546* (2013.01); *A61B 5/157* (2013.01); *A61B 5/1519* (2013.01); *A61B 5/150022* (2013.01); *A61B 5/15087* (2013.01); *A61B 5/15113* (2013.01); *A61B 5/150175* (2013.01); *A61B 5/150358* (2013.01); *A61B 5/150412* (2013.01); *A61B 5/150503* (2013.01); *A61B 5/150824* (2013.01); *G01N 33/48792* (2013.01); *A61B 5/14532* (2013.01)

(56) References Cited

U.S. PATENT DOCUMENTS

| | | |
|---|---|---|
| 2003/0050627 A1 | 3/2003 | Taylor et al. |
| 2003/0083686 A1 | 5/2003 | Freeman et al. |
| 2003/0176183 A1 | 9/2003 | Drucker et al. |
| 2004/0138588 A1 | 7/2004 | Saikley et al. |
| 2005/0159678 A1 | 7/2005 | Tanniike et al. |

OTHER PUBLICATIONS

Written Opinion of the International Searching Authority corresponding to co-pending International Patent Application No. PCT/US2005/044802, European Patent Office, dated Apr. 13, 2006, 7 pages.

International Search Report corresponding to co-pending International Patent Application No. PCT/US2005/044802, European Patent Office, dated Apr. 13, 2006, 6 pages.

MARKER FOR READINGS TAKEN FROM ALTERNATIVE SITE TESTS

CROSS-REFERENCE TO RELATED APPLICATIONS

This application is a continuation of U.S. application Ser. No. 11/792,322, filed on Jun. 4, 2007, which is a U.S. National Phase Filing of International Application No. PCT/US2005/044802, filed Dec. 12, 2005, which is related to and claims priority to U.S. Provisional Application No. 60/635,574, filed Dec. 13, 2004, the contents of these applications being incorporated entirely herein by reference.

FIELD OF THE INVENTION

The present invention relates generally to fluid sample testing and, more particularly, to a system and method for distinguishing test results obtained from alternative-test-site fluid samples from standard-test-site fluid samples.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets.

Those who have irregular blood glucose concentration levels are medically required to regularly self-monitor their blood glucose concentration level. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and they may eventually faint. A person can also become very ill if their blood glucose level becomes too high—a condition known as hyperglycemia. Both conditions, hypoglycemia and hyperglycemia, are potentially life-threatening emergencies.

One method of monitoring a test subject's blood glucose level is with a portable, hand-held blood glucose testing device. In order to check the blood glucose level with the testing device, a drop of blood is obtained from the fingertip using a lancing device. A typical lancing device contains a needle lancet to puncture the skin of a finger. This monitoring procedure often is repeated several times a day. Because this procedure can be painful, instruments have been developed to obtain blood from alternate sites other than a fingertip such as arms, legs and palm of the hand. Although obtaining a blood sample from an alternate site is less painful, Alternative Site Testing (AST) results in intrinsic testing problems that have not previously been addressed.

Typically, the test subject uses the hand-held blood testing device to determine the glucose concentration in the blood sample. The test subject then writes the determined concentration into a log book along with other information, such as the date and time. This log book is then provided to a physician or other health care professional who analyzes the provided data to determine the proper course of action for the test subject. Thus, if the data in the log book is flawed, the diagnosis and course of action generally will be flawed as well.

Utilizing AST increases the potential for improper glucose concentrations to be obtained. For example, to help ensure a proper determination of the glucose concentration, AST should not be used for approximately two hours after a meal, insulin injection, or exercise. Though test subjects are generally informed of these precautions by their health care professional(s), test subjects have been known to disregard or forget these precautions. Thus, even if the test subject properly utilizes the blood testing device and accurately records the data into their log book, the data may still be flawed.

Therefore, there exists a need for a system that distinguishes an alternative-site test result from a standard-site test result.

SUMMARY OF THE INVENTION

A meter for determining the concentration of an analyte in a fluid sample is disclosed, according to one embodiment of the present invention. The meter includes a memory device adapted to store information and an electrical circuitry adapted to determine the analyte concentration of the fluid sample located on a test sensor. The electrical circuitry is in electronic communication with the memory device and communicates the determined analyte concentration to the memory device for storage. The meter further includes a means for distinguishing an alternative site test from a standard site test.

According to another embodiment of the present invention, a meter for determining the concentration of an analyte in a fluid sample is disclosed. The meter includes a memory device adapted to store information and an electrical circuitry adapted to determine the analyte concentration of the fluid sample located on a test sensor. The electrical circuitry is in electronic communication with the memory device and communicates the determined analyte concentration to the memory device for storage. The meter further includes a detection device adapted to detect when the meter is being used for an alternative site test. The detection device is in electronic communication with the memory device and electrical circuitry. The determined analyte concentration is stored in the memory device along with a marker indicating whether the fluid sample was obtained from an alternative test site.

According to yet another embodiment of the present invention, an integrated meter for determining the concentration of an analyte in a fluid sample is disclosed. The integrated meter includes a lancing mechanism incorporated into the above disclosed meter. The lancing mechanism is adapted to assist in the collection of the fluid sample. The lancing mechanism includes an endcap and a removably attachable lance disposed at least partially therein.

According to one embodiment of the present invention a method for determining an analyte concentration in a fluid sample is disclosed. The method includes the act of providing a meter adapted to determine the analyte concentration in the fluid sample after the fluid sample has been applied to a test sensor. The meter has a memory device adapted to store information. The method further includes the act of providing a lancing mechanism including at least one removeably attachable endcap. The method further includes the acts of attaching the at least one endcap to the lancing mechanism and collecting the fluid sample by lancing the skin of a test subject with a lance removably attached to the lancing mechanism. The method further includes the acts of detecting whether an alternative test site is being lanced by the lancing mechanism and applying the collected fluid sample to the test sensor. The method further includes the acts of determining the analyte concentration in the applied fluid sample, storing the determined analyte concentration in the memory device, and marking the determined analyte concentration as being collected from the alternative test site. The marker is linked to the determined analyte concentration.

According to another embodiment of the present invention, a method for determining an analyte concentration in a fluid sample is disclosed. The method includes the act of providing a meter having (i) a memory device adapted to store information, (ii) an electrical circuitry adapted to determine the analyte concentration of the fluid sample located on a test sensor, and (iii) means for distinguishing an alternative site test from a standard site test. The electrical circuitry of the meter is in electronic communication with the memory device and communicates the determined analyte concentration to the memory device for storage. The method further includes the act of marking the determined analyte concentration with a marker. The marker is linked to the determined analyte concentration. The marker distinguishes the determined analyte concentration as being from the fluid sample collected from either an alternative test site or a standard test site.

The above summary of the present invention is not intended to represent each embodiment, or every aspect, of the present invention. Additional features and benefits of the present invention are apparent from the detailed description and figures set forth below.

DESCRIPTION OF ILLUSTRATED EMBODIMENTS

The present invention is directed to a system and method for distinguishing between an analyte concentration obtained via an Alternative-Site Test (AST) and an analyte concentration obtained via a Standard-Site Test (SST). The analyte concentrations may then be marked with at least one marker to distinguish the AST results from the SST results. Analyte concentrations that may be marked using the present invention include, for example, glucose, lipid profiles (e.g., cholesterol, triglycerides, LDL and HDL), microalbumin, hemoglobin $A_1C$, fructose, lactate, bilirubin, or prothrombin. The present invention is not limited, however, to these specific analytes and it is contemplated that other analyte concentrations may be marked. The analytes may be in, for example, a whole blood sample, a blood serum sample, a blood plasma sample, other body fluids like ISF (interstitial fluid) and urine, or other non-body fluid samples.

Figure 1:
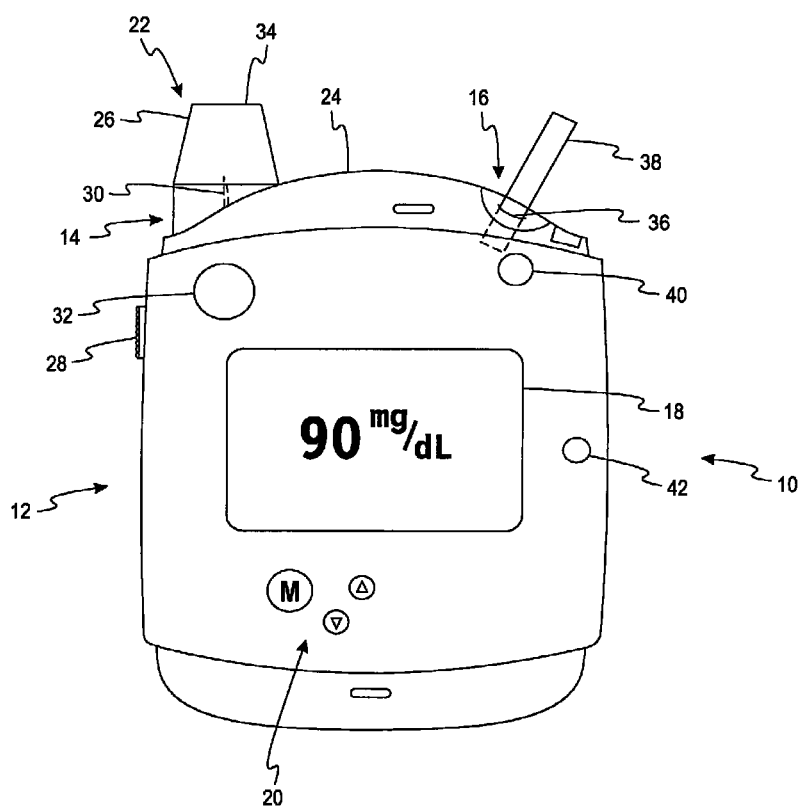
FIG. 1 is a top view of an integrated meter, according to one embodiment of the present invention.

Turning now to the drawings and initially to FIG. 1, an integrated meter 10 is illustrated that may be used in combination with the present invention. The integrated meter 10 comprises a housing 12, a lancing mechanism 14, a testing mechanism 16, a display 18, and a button set 20. An external portion 22 of the lancing mechanism 14 is located on a testing end 24 of the housing 12. The lancing mechanism 14 is partially enclosed within the housing 12 with a lancing endcap 26 removably attached to the external portion 22 of the lancing mechanism 14 opposite the housing 12. A slider 28 is located on the exterior of the housing 12 and is operatively connected to the lancing mechanism 14 so as to cock the lancing mechanism 14.

The lancing mechanism 14 is used to lance the skin of a test subject with a removably attached lance 30 (e.g., a lancet). The lancing endcap 26 has a central aperture and protects the test subject from inadvertently contacting the lance 30 located therein. The lance 30 is adapted to obtain a fluid sample from the test subject. In use, the slider 28 is utilized to cock the lancing mechanism 14—moving the lance 30 further into the housing 12. A firing button 32 is provided on the exterior of the housing 12 that, when depressed, fires the cocked lancing device 14. A face 34 of the endcap 26 can be touched to the skin of the test subject. The lancing device 14 can then be fired (by depressing the firing button 32) causing the lance 30 to extend from the endcap 26 and pierce the skin of the test subject. The lancing mechanism 14 is adjacent to the testing mechanism 16 for convenient side-by-side lancing and testing that reduces the required level of component manipulation by the user. As illustrated in FIG. 1, the testing mechanism 16 is angularly aligned on the meter 10 to facilitate an AST. However, the location and interaction of the components of the integrated meter 10 may vary and a more detailed description of the various configurations is not necessary to understand the present invention.

The testing mechanism 16 includes a test-sensor opening 36 formed in the testing end 24 of the housing 12. The test-sensor opening 36 is adapted to seat a test sensor 38 therein. The test sensor 38 contains at least one reagent located thereon that is adapted to react with an analyte of interest within a fluid sample. The test sensor 38 may be seated in the test-sensor opening 36 by the test subject, or may be dispensed and seated in the test-sensor opening 36 from within the integrated meter 10. Once seated, the test sensor 38 is connected to electrical circuitry (not shown) within the integrated meter 10 that is adapted to perform an electrochemical determination of the concentration of an analyte in a fluid sample. An ejection mechanism 40 is provided to allow the test subject to remove the test sensor 38 from the integrated meter 10 once the fluid sample analysis has been performed.

The display 18 is used to display the determined concentration and provide other information to the test subject. As will be discussed below, the display may also be used to indicate to a user that an AST or a SST is being or has been performed. The test subject may interact with the integrated meter 10 by utilizing the button set 20.

As discussed above, the integrated meter 10 includes electrical circuitry (not shown). The electrical circuitry includes various electronics and electrical components used to operate the integrated meter 10. The electrical circuitry is connected to the display 18 as well as the testing mechanism 16. Further, the electrical circuitry is communicatively coupled to a memory device (not shown). The memory device is adapted to store information such as determined analyte concentrations, whether the fluid sample was collected from an alternative test site, date and time information, etc. The memory device is typically a nonvolatile memory, such as, for example, EPROM (erasable programmable read-only memory) or EEPROM (electrically erasable programmable read-only memory). A battery (not shown) is used to power the electrical circuitry and display 18 within the integrated meter 10.

The electrical circuitry can include a communications interface 42 adapted to allow the integrated meter 10 to communicate with an external device (e.g., computer, laptop, personal digital assistant, remote server, a network-connected device, etc.). The communications interface 42 allows the external device to access at least the analyte concentrations stored in the memory device. The communication interface 42 can be any number of devices that allow the integrated meter 10 to communicate with an external device, such as, for example, a standard serial port, an infra-red emitter/detector port, a telephone jack, a radio frequency transmitter/receiver port, modem, etc. The electrical circuitry may also include ROM chips for carrying out programs.

The lancing mechanism 14 of the integrated meter 10 is adapted to utilize a plurality of lancing endcaps 26. For example, a test subject can attach a SST endcap when the test subject prefers to collect a sample from their fingertip. Alternatively, an AST endcap can be attached to the lancing mechanism 14 when an AST is desired. Typically, an AST endcap is transparent to allow the test subject to look through the endcap to determine the volume of blood that is collected after lancing the skin. The AST endcap may also have a wider opening to allow more skin to insert therein, thus allowing for a deeper lancing of the skin.

The lancing mechanism 14 includes a detection device (not shown)—that may have one or more type of sensor incorporated therein—to detect when an AST endcap (or in other embodiments a SST endcap) has been attached. For example, according to one embodiment the detection device of the lancing mechanism 14 contains at least one sensor to detect electrical contacts on an AST endcap. In this embodiment, the AST endcap contains at least one electrical contact thereon. The contact can then be detected by the sensor to determine that an AST endcap is being used. The SST endcap (adapted to allow standard fingertip lancing) may contain contacts arranged in a different configuration or may be contact free. Alternatively, at least one contact may be located on an AST lance that can be detected by the sensor to determine that an AST is being performed.

In another embodiment, the meter includes at least two lancing mechanisms. The first lancing mechanism is designed to allow a test subject to lance a fingertip, while the second lancing mechanism is designed to allow a test subject to lance an alternative-test site. In this embodiment one or both of the lancing mechanisms may contain a pressure sensor that is adapted to detect when an endcap 26 or lance 30 is attached to the lancing mechanism. Thus, if an endcap 26 or lance 30 is attached to the alternative-test site lancing mechanism, the detection device determines that an AST is being performed.

In yet another embodiment, the detection device of the lancing mechanism 14 contains one or more optical sensor. In this embodiment, the AST endcap and the SST endcap may be made of different materials. For example, the AST endcap may be made of a more optically clear material than the SST endcap, such that when the SST endcap is attached, the optical sensor detects the presence of the endcap and the detection device determines that an AST is not being performed. Alternatively, the optical sensor may be used to detect that an AST lance or an SST lance has been removeably attached to the lancing mechanism 14.

In another embodiment of the present invention, the detection device of the lancing mechanism 14 includes a depth sensor (not shown) that is adapted to determine the depth of puncture that the lance 30 will produce. In this embodiment, the depth sensor determines the distance that the lance 30 extends from the face 34 of the endcap 26. The depth of puncture is typically indicative of whether an alternative test site on a test subject is being lanced. When the depth sensor detects that the lance 30 is extending further than a predetermined threshold, the detection device sends a communication to the electronic circuitry and/or memory device to indicate that an AST is being performed. The lancing mechanism 14 may also allow the threshold to be customized to the test subject to suit the individual needs of the test subject.

Figure 2:
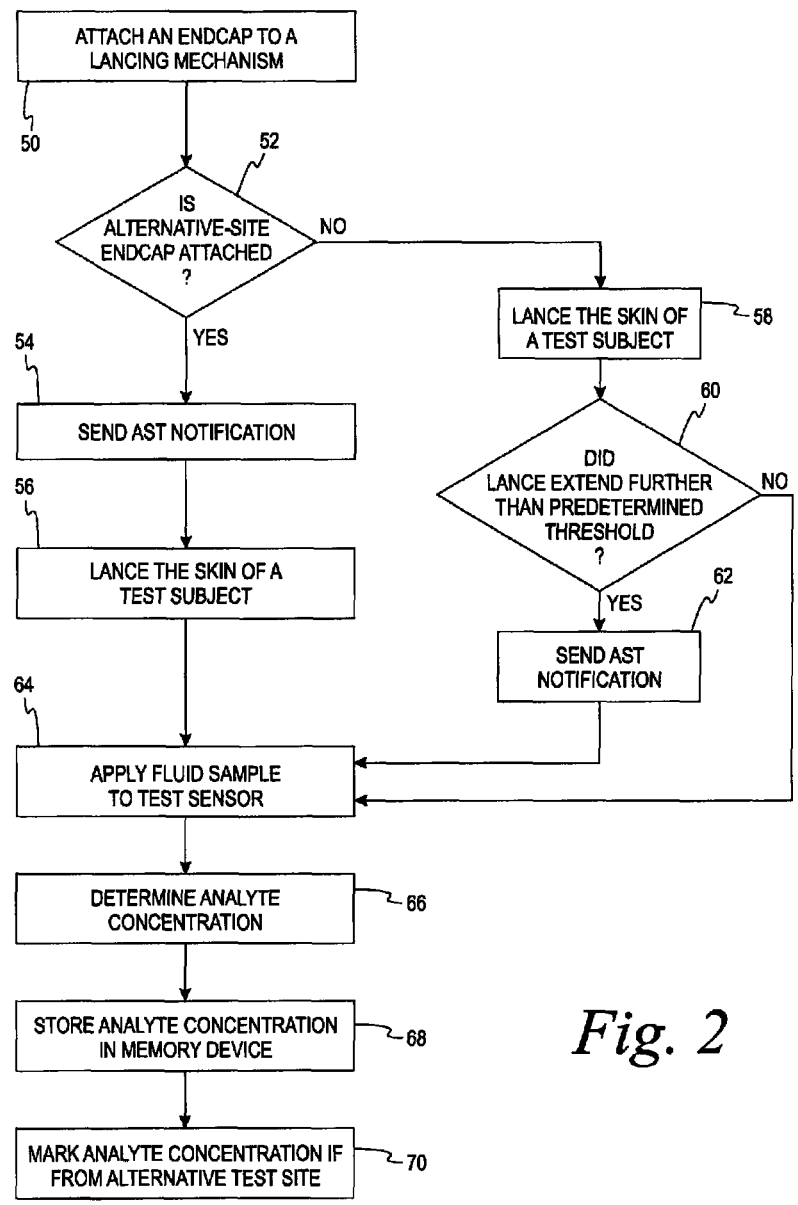
FIG. 2 is a flowchart illustrating a method of marking an analyte concentration as being collected from an alternative test site, according to one embodiment of the present invention.

Referring also to FIG. 2, a method for marking an analyte concentration determined from a fluid sample collected from an alternative test site is illustrated, according to one embodiment of the present invention. Initially, an endcap 26 is removeably attached to the lancing mechanism 14, at step 50. The endcap 26 may be an AST endcap, a SST endcap, or another type of endcap. At decision box 52, a determination is made as to whether the attached endcap is an AST endcap. This determination is made by the detection device included in the lancing mechanism. If the determination is made, at decision box 52, that an AST endcap has been attached, an AST notification is sent to the electrical circuitry and/or memory device of the meter, at step 54. The test subject then utilizes the lancing mechanism to lance their skin, at step 56. Alternatively, if at step 52, the decision is made that an AST endcap has not been attached—or a determination is not made at all—the test subject lances their skin, at step 58. Once the test subject has lanced their skin at step 58, a determination is made by the detection device, at decision box 60, whether the lance 30 extended further than a predetermined (or customized) threshold. If the detection device determines that the lance 30 did extend past the predetermined threshold (indicating that an alternative test site was lanced by the test subject), an AST notification is sent to the electrical circuitry and/or memory device of the meter, at step 62.

After the test subject has lanced their skin at step 56 or step 58, the collected fluid sample is applied to a test sensor, at step 64. The meter then, at step 66, determines the analyte concentration of the fluid sample that has been applied to the test sensor. The analyte concentration determined at step 66 is stored to the memory device, at step 68. Additionally, if an AST notification has been sent by the detection device at step 54 or step 62, the analyte concentration stored into the memory device at step 68 is marked with an AST marker, at step 70, that is linked to the analyte concentration.

The marker may be linked or coupled to the stored analyte concentration by any means known in the art. Suffice it to say, that when an analyte concentration has been marked with an AST marker, the AST marker will be made apparent to the test subject on the display of the meter. Additionally or alternatively, the AST marker will appear with the associated analyte concentration if the information contained on the memory device is downloaded or otherwise communicated to an external device via the communication interface 42.

Figure 3:
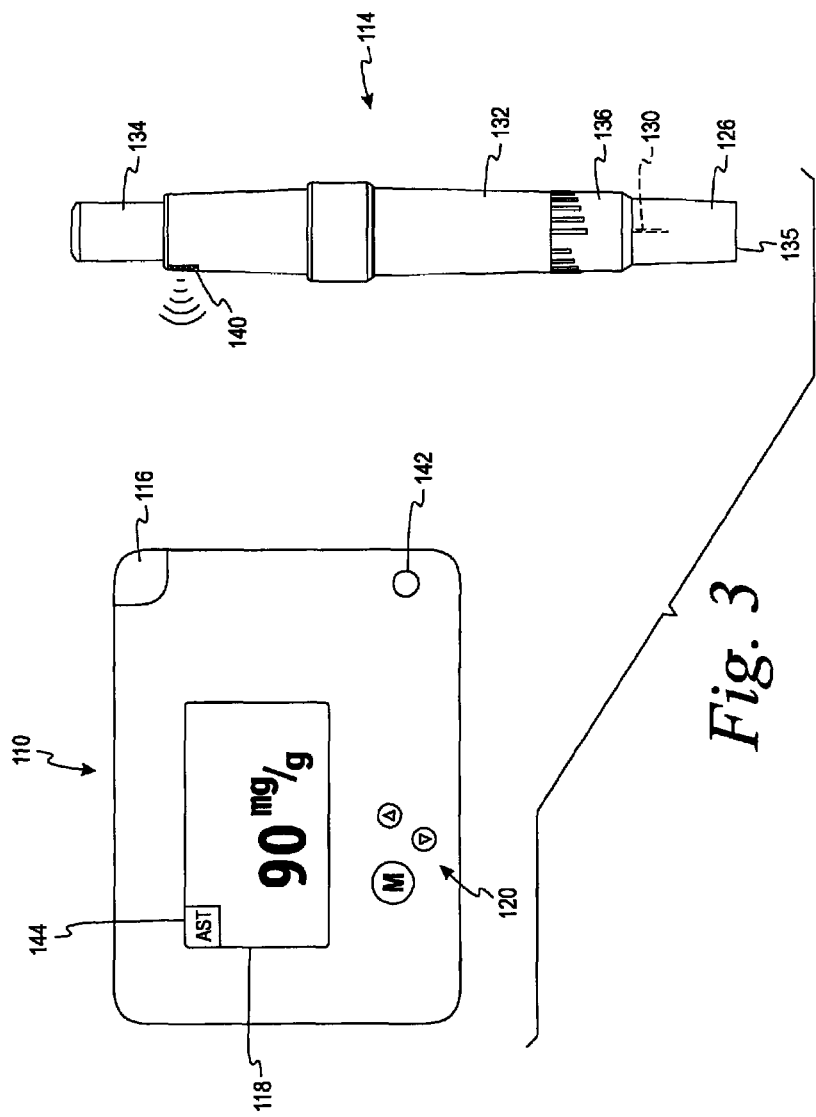
FIG. 3 is a top view of a meter and a lancing mechanism, according to another embodiment of the present invention.

Turning now to FIG. 3, a meter 110 and separate lancing mechanism 114 are illustrated according to another embodiment of the present invention. The meter 110 and lancing mechanism 114 are operative in much the same way as the integrated meter 10 described above with respect to FIG. 1. The meter 110 and lancing mechanism 114 are adapted to assist in performing the method for distinguishing between an analyte concentration determined from an AST fluid sample and from an SST fluid sample, as described above with respect to FIG. 2.

The illustrated meter 110 comprises an optical read-head 116, a display 118, a button set 120, a communications interface 142, and a detection device (not shown). The optical read-head 116 is adapted to optically determine an analyte concentration of a fluid sample. Though, as is readily apparent from the above discussion, the manner in which the analyte concentration is determined is not of importance to the AST or SST marking of the present invention. Thus, a meter or integrated meter utilizing any number of methods (e.g., optically, electrochemically, viscosimetrically, thermally, etc.) to determine the concentration of analyte in a fluid sample may be incorporated into the present invention.

The lancing mechanism 114 comprises an endcap 126 with a removeably attachable lance 130 partially disposed therein. The endcap 126 is attached to the housing 132 of the lancing mechanism 114 opposite an actuator 134. The actuator 134 is adapted to cause the lance 130 to extend from the face 135 of the endcap 126 and puncture the test subjects skin. An adjustment mechanism 136 is provided to adjust the depth that the lance 130 is able to extend from the face 135 of the endcap 126.

The lancing mechanism 114 also comprises an external detection device (not shown) that is adapted to determine whether an alternative test site or a standard test site is to be punctured on the test subject. The external detection device is located within the lancing mechanism 114 and is separate from the meter 110. The external detection device is coupled to a communication interface 140 located on the lancing mechanism 114. The communication interface 140 may be one or more of a variety of types, such as an infra-red emitter/detector port, a radio frequency transmitter/receiver port, a standard serial port, a telephone jack, etc. The communication interface 140 is adapted to communicate with a detection device (not shown) in the meter 110.

The detection device of the meter 110 is adapted to receive the communication for the external detection device of the lancing mechanism 114, and communicate the communication to one or both of the electrical circuitry and memory device of the meter 110. Thus, when the external detection device determines that an alternative test site is being lanced, the communication interface 140 provides this information to the meter 110 that can then mark the analyte concentration, once determined, as being collected from an alternative test site or a standard test site.

The external detection device of the lancing mechanism 114 may be of the type described above with respect to the detection device of the integrated meter 10, illustrated in FIG. 1. Additionally or alternatively, the detection device may be adapted to monitor the adjustment mechanism 136 to determine whether an AST or SST is being performed. For example, the adjustment mechanism 136 may include an AST position that a test subject may use to perform an AST. Typically, the AST position is designed to allow the lance 130 to further extend from the face 135 of the endcap 126, thus piercing further into the skin of the test subject. By utilizing the adjustment mechanism 136, a single endcap 126 may be utilized to perform both an AST and a SST. In these embodiments, the endcap 126 may be removeably attachable to the housing 132 of the lancing mechanism 114 or may be permanently fixed thereto.

As illustrated in FIG. 3, the display 118 may include a marker portion 144 that indicates that the displayed analyte concentration is from an AST. In addition or as an alternative to the above described marking method, the button set 120 may be adapted to allow a test subject to manually mark an analyte concentration as being from an AST. In other embodiments, an additional button is added to the button set and is provided solely to allow a user to manually mark an analyte concentration as being from an alternative test site, as illustrated in FIG. 4.

Figure 4:
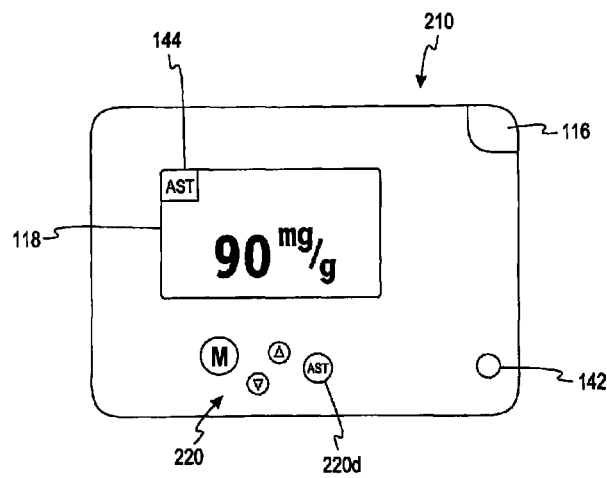
FIG. 4 is a top view of a meter having an AST button, according to yet another embodiment of the present invention.

FIG. 4 illustrates a meter 210 that includes an AST button 220d in a button set 220. The AST button 220d is adapted to allow a test subject to distinguish an AST from a SST. In this embodiment, the default test mode for the meter 210 is set as a SST. Thus, when the meter 210 is activated (e.g., turned on), the meter 210 will expect that a fluid sample will be collected from a standard test site. However, if a test subject plans to perform an AST, the test subject depresses the AST button 220d to communicate to the meter that this fluid sample that will be analyzed is from an alternative test site. Depressing the AST button 220d a second time will toggle the meter 210 back into the default SST mode.

The meter 210 is similar to the meter 110 of FIG. 3 in design and includes a detection device (not shown) in some embodiments. In other embodiments, the AST button 220d is the sole means for distinguishing an AST from a SST. In yet other embodiments, the AST button 220d is replaced with a SST button and the default test mode is set to AST.

Figure 5:
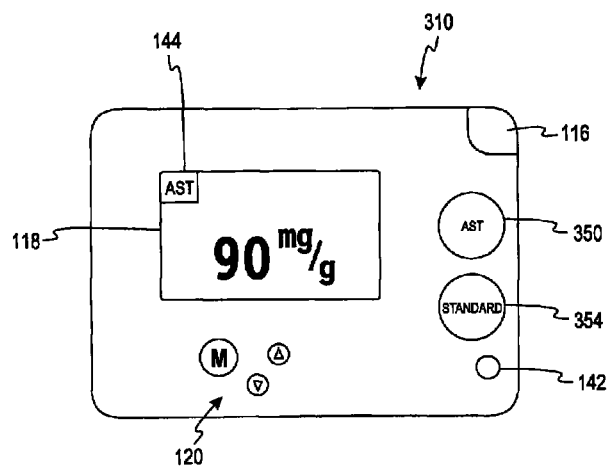
FIG. 5 is a top view of a meter having a plurality of endcap docking stations, according to one embodiment of the present invention.

Turning now to FIG. 5, a meter 310 is illustrated according to one embodiment of the present invention. The meter 310 includes a plurality of endcap docking stations 350, 354 that are each adapted to seat an endcap. In one embodiment, the AST-endcap docking station 350 that seats the AST endcap is slightly larger than the SST endcap docking station 354. In other embodiments, where both the AST endcap and the SST endcap are the same (or of similar) size, as illustrated in FIG. 5, the endcap docking stations 350, 354 may be visually distinguished with text, as illustrated in FIG. 5. In yet other embodiments of the present invention, a portion of the endcap—that is seated in the endcap docking stations 350, 354—is uniquely shaped to distinguish an AST endcap from a SST endcap. In these embodiments, the endcap docking stations 350, 354 are shaped so as to allow only an AST endcap to be seated in the AST-endcap docking station 350 and only allow a SST endcap to be seated in the SST-endcap docking station 354. The endcap docking stations 350, 354 may be distinguishable in other ways, such as, by color, by texture, by location, etc.

The meter 310 includes at least one detection device (not shown) that detects when an endcap is removed from one of the endcap docking stations 350, 354. For example, if a test subject removes the AST endcap from the AST-endcap docking station 350, the detection device detects the removal of the AST endcap and communicates the removal to the electrical circuitry of the meter 310. Thus, the meter 310 determines that an AST is being performed and can link the determined analyte concentration with an AST marker. Alternatively, the detection device may detect the removal of the SST endcap from the SST-endcap docking station 354. In this embodiment, the meter 310 determines that a SST is being performed. The detection device may be any of the variety of detection devices described above with respect to the meter 10, illustrated in FIG. 1. In some embodiments, the meter 310 is configured to prohibit testing if both the SST-endcap and the AST-endcap are removed from the endcap docking stations 350, 354.

In other embodiments of the present invention, a single endcap docking station is formed in the meter 310. In these embodiments, the detection device determines when the endcap is removed from the endcap docking station and communicates the removal to the electronic circuitry. The meter 310 then determines whether an AST or SST is being performed based on whether the endcap docking station is adapted to seat an AST endcap or a SST endcap. The meter 310 then marks the determined analyte concentration with an appropriate marker (where necessary) and links the marker to the determined analyte concentration stored in the memory device.

It should be readily apparent from the above discussion, that a marker is linked to a determined analyte concentration to distinguish a result from an AST from a result from a SST. In some embodiments of the present invention, an AST marker is used and linked to analyte concentrations determined from alternative-test-site fluid samples. While in other embodiments, a SST marker is used and linked to analyte concentrations determined from standard-test-site fluid samples. In yet other embodiments, either an AST marker or a SST marker is linked to each of the determined analyte concentrations depending on where the fluid sample was collected from. As is apparent to one skilled in the art, the marking system may be any of the above described systems, or obvious variations thereof, sufficient to distinguish an AST analyte concentration from a SST analyte concentration.

The electrical circuitry of the above meters may also include a calendar device to track the time and/or date that a measurement is taken. The calendar device may be, for example, a real-time clock adapted to electronically communicate date and time information to the memory device. The date and time information can be linked to ("time stamped") the determined analyte concentration. The date and time information may be used to flag suspect analyte concentrations where an AST test would not be appropriate.

For example, an AST is not recommended to be performed within two hours of eating a meal due to fluctuations in the analyte concentrations during this interval. The meter may be programmed to assume that when a test subject performs a fluid sample test between the hours of 11:00 a.m.-12:30 p.m. that they are performing a pre-meal test. If a test subject then performs a second test within two hours of the first test, and the second test is determined to be an AST, the meter would flag the determined analyte concentration as being suspect. In addition to flagging the data, the meter may sound an alarm warning the test subject that an AST is not recommended at this time. By utilizing the time information, and flagging the suspect determination thereafter, the meter assists the test subject in remembering to follow the guidelines for an AST. Additionally, a heath care professional could later view the flag and remind the test subject of the AST guidelines and could reeducate the test subject accordingly.

Alternative Embodiment A

A meter for determining the concentration of an analyte in a fluid sample, the meter comprising:
a memory device adapted to store information;
an electrical circuitry adapted to determine the analyte concentration of the fluid sample located on a test sensor, the electrical circuitry being in electronic communication with the memory device, the electrical circuitry communicating the determined analyte concentration to the memory device for storage; and
means for distinguishing an alternative site test from a standard site test.

Alternative Embodiment B

The meter of Alternative Embodiment A wherein the determined analyte concentration is marked with an AST marker when the fluid sample is obtained from an alternative test site.

Alternative Embodiment C

The meter of Alternative Embodiment A wherein the determined analyte concentration is marked with a marker when the fluid sample is obtained from a standard test site.

Alternative Embodiment D

The meter of Alternative Embodiment A further comprising a button set adapted to allow a test subject to distinguish an alternative site test from a standard site test.

Alternative Embodiment E

The meter of Alternative Embodiment D wherein the button set includes an individual button adapted to allow the test subject to distinguish an alternative site test from a standard site test.

Alternative Embodiment F

The meter of Alternative Embodiment A further comprising a communications interface in communication with at least one of the electrical circuitry and the memory device, the communications interface adapted to communicate information provided by at least one of the electrical circuitry and the memory device to an external device.

Alternative Embodiment G

The meter of Alternative Embodiment F wherein the communicated information includes at least one determined analyte concentration.

Alternative Embodiment H

The meter of Alternative Embodiment G wherein the communicated information includes an AST marker linked to the at least one determined analyte concentration when the at least one determined analyte concentration was obtained from an alternative test site.

Alternative Embodiment I

The meter of Alternative Embodiment G wherein the communicated information includes a date and time stamp linked to each of the at least one determined analyte concentration.

Alternative Embodiment J

The meter of Alternative Embodiment A wherein a detection device distinguishes an alternative site test from a standard site test.

Alternative Embodiment K

The meter of Alternative Embodiment J further comprising at least one endcap docking station formed in the meter, the endcap docking station being adapted to seat at least one endcap for storage therein.

Alternative Embodiment L

The meter of Alternative Embodiment K wherein the detection device detects when an AST endcap has been removed from the at least one endcap docking station.

Alternative Embodiment M

The meter of Alternative Embodiment L wherein the determined analyte concentration is marked with an AST marker when the detection device detects that the AST endcap has been removed from the at least one endcap docking station.

Alternative Embodiment N

The meter of Alternative Embodiment K wherein the detection device detects when a SST endcap has been removed from the at least one endcap docking station.

Alternative Embodiment O

The meter of Alternative Embodiment N wherein the determined analyte concentration is marked with a marker when the detection device detects that the SST endcap has been removed from the at least one endcap docking station.

Alternative Embodiment P

A meter for determining the concentration of an analyte in a fluid sample, the meter comprising:
  a memory device adapted to store information;
  an electrical circuitry adapted to determine the analyte concentration of the fluid sample located on a test sensor, the electrical circuitry being in electronic communication with the memory device, the electrical circuitry communicating the determined analyte concentration to the memory device for storage; and
  a detection device adapted to detect when the meter is being used for an alternative site test, the detection device being in electronic communication with the memory device and electrical circuitry,
  wherein the determined analyte concentration is stored in the memory device along with a marker indicating whether the fluid sample was obtained from an alternative test site.

Alternative Embodiment Q

The meter of Alternative Embodiment P wherein the electrical circuitry includes a read-head for optically determining the concentration of the analyte.

Alternative Embodiment R

The meter of Alternative Embodiment P wherein the electrical circuitry electrochemically determines the concentration of the analyte.

Alternative Embodiment S

The meter of Alternative Embodiment P wherein the detection device communicates to one or more of the electrical circuitry and memory device when the alternative site test has been detected.

Alternative Embodiment T

The meter of Alternative Embodiment P wherein the detection device communicates to one or more of the electrical circuitry and memory device when a standard site test has been detected.

Alternative Embodiment U

The meter of Alternative Embodiment P wherein the meter is adapted to be used with a lancing mechanism, the detection device detecting when an AST endcap has been removably attached to the lancing mechanism.

Alternative Embodiment V

The meter of Alternative Embodiment P wherein the meter is adapted to be used with a lancing mechanism, the detection device detecting the distance a lance extends from the lancing mechanism to determine whether an alternative test site is being lanced.

Alternative Embodiment W

The meter of Alternative Embodiment P wherein the detection device of the meter is in communication with an external detection device, the external detection device being located in a lancing mechanism, the external detection device being adapted to communicate to the detection device of the meter when the lancing mechanism is being used to obtain a fluid sample from an alternative test site.

Alternative Embodiment X

The meter of Alternative Embodiment W wherein the detection device of the meter is an infra-red detector and the external detection device includes an infra-red emitter.

Alternative Embodiment Y

The meter of Alternative Embodiment W wherein the detection device of the meter is a radio frequency receiver and the external detection device includes a radio frequency transmitter.

Alternative Embodiment Z

The meter of Alternative Embodiment P wherein the electrical circuitry includes a real-time clock adapted to electronically communicate date and time information to the memory device, the date and time information being stored in the memory device along with the determined analyte concentration.

Alternative Embodiment AA

The meter of Alternative Embodiment P further comprising a display adapted to display information provided by one or more of the electrical circuitry and memory device.

Alternative Embodiment AB

The meter of Alternative Embodiment P wherein the electrical circuitry includes a communication interface adapted to communicate information provided by one or more of the electrical circuitry and memory device to an external device.

Alternative Embodiment AC

The meter of Alternative Embodiment P wherein the meter is adapted to be used with a lancing mechanism, the detection device detecting when an AST lance has been removably attached to the lancing mechanism.

Alternative Embodiment AD

The meter of Alternative Embodiment P wherein the meter is adapted to be used with a lancing mechanism, the detection device detecting when an SST lance has been removably attached to the lancing mechanism.

Alternative Embodiment AE

The meter of Alternative Embodiment P wherein the meter is adapted to be used with a lancing mechanism adapted to removeably attach to a lance, the lancing mechanism including an adjustment mechanism for adjusting the puncture depth of the lance, the detection device detecting when an AST puncture depth has been selected.

Alternative Embodiment AF

An integrated meter for determining the concentration of an analyte in a fluid sample, the integrated meter comprising:
a lancing mechanism adapted to assist in the collection of the fluid sample, the lancing mechanism including an endcap and a removably attachable lance disposed at least partially therein;
a memory device adapted to store information;
an electrical circuitry adapted to determine the analyte concentration of the fluid sample located on a test sensor, the electrical circuitry being in electronic communication with the memory device, the electrical circuitry communicating the determined analyte concentration to the memory device for storage; and
a detection device adapted to detect when the lancing device is being used to assist in the collection of the fluid sample from an alternative test site, the detection device being in electronic communication with the memory device and electrical circuitry,
wherein the determined analyte concentration is stored in the memory device along with a marker indicating that the fluid sample was obtained from the alternative test site.

Alternative Embodiment AG

The integrated meter of Alternative Embodiment AF wherein the endcap is removably attachable to the lancing mechanism.

Alternative Embodiment AH

The integrated meter of Alternative Embodiment AG wherein the detection device detects when an AST endcap has been removably attached to the lancing mechanism.

Alternative Embodiment AI

The integrated meter of Alternative Embodiment AG wherein the detection device detects when a SST endcap has been removably attached to the lancing mechanism.

Alternative Embodiment AJ

The integrated meter of Alternative Embodiment AI wherein the detection device communicates to one or more of the electrical circuitry and memory device when a standard site test has been detected.

Alternative Embodiment AK

The integrated meter of Alternative Embodiment AF wherein the detection device detects the distance the lance extends from the lancing mechanism to determine whether an alternative test site is being lanced.

Alternative Embodiment AL

The integrated meter of Alternative Embodiment AF wherein the electrical circuitry includes a real-time clock adapted to electronically communicate date and time information to the memory device, the date and time information being stored in the memory device along with the determined analyte concentration.

Alternative Embodiment AM

The integrated meter of Alternative Embodiment AF wherein the electrical circuitry includes a communication interface adapted to communicate information provided by one or more of the electrical circuitry and memory device to an external device.

Alternative Embodiment AN

The integrated meter of Alternative Embodiment AF wherein the detection device communicates to one or more of the electrical circuitry and memory device when the alternative site test has been detected.

Alternative Process AO

A method for determining an analyte concentration in a fluid sample, the method comprising the acts of:
providing a meter adapted to determine the analyte concentration in the fluid sample after the fluid sample has been applied to a test sensor, the meter having a memory device adapted to store information;
providing a lancing mechanism including at least one removeably attachable endcap;
attaching the at least one endcap to the lancing mechanism;
collecting the fluid sample by lancing the skin of a test subject with a lance removably attached to the lancing mechanism;
detecting whether an alternative test site is being lanced by the lancing mechanism;
applying the collected fluid sample to the test sensor;
determining the analyte concentration in the applied fluid sample;
storing the determined analyte concentration in the memory device; and marking the determined analyte concentration as being collected from the alternative test site, the marker being linked to the determined analyte concentration.

Alternative Process AP

The method of Alternative Process AO further comprising the act of downloading the stored, determined analyte concentration to a separate device via a communication interface provided with the meter.

Alternative Process AQ

The method of Alternative Process AO wherein the detecting of the lancing of the alternative test site is performed by detecting whether an AST endcap has been removeably attached to the lancing mechanism.

Alternative Process AR

The method of Alternative Process AQ wherein the detecting of the AST endcap is performed by detecting at least one electrical contact provided with the AST endcap.

Alternative Process AS

The method of Alternative Process AQ wherein the detecting of the AST endcap is performed by detecting when the AST endcap is applied to an alternative-site seat on the lancing mechanism.

Alternative Process AT

The method of Alternative Process AO wherein the detecting of the lancing of the alternative test site is performed by detecting the depth of lancing of the test subject's skin.

Alternative Process AU

The method of Alternative Process AO wherein the lancing mechanism is separate from the meter.

Alternative Process AV

The method of Alternative Process AU further comprising communicating to the meter via an external detection device of the lancing mechanism that the lancing is being performed at the alternative test site.

Alternative Process AW

The method of Alternative Process AU further comprising communicating to the meter via an external detection device of the lancing mechanism that the lancing is being performed at a standard site.

Alternative Process AX

The method of Alternative Process AO wherein the determination of the analyte concentration in the applied fluid sample is performed optically.

Alternative Process AY

The method of Alternative Process AO wherein the determination of the analyte concentration in the applied fluid sample is performed electrochemically.

Alternative Process AZ

The method of Alternative Process AO further comprising:
providing a real-time clock adapted to electronically communicate date and time information to the memory device,
storing the date and time information in the memory device, the date and time information being linked to the determined analyte concentration.

Alternative Process BA

A method for determining an analyte concentration in a fluid sample, the method comprising the acts of:
providing a meter having
(i) a memory device adapted to store information,
(ii) an electrical circuitry adapted to determine the analyte concentration of the fluid sample located on a test sensor, the electrical circuitry being in electronic communication with the memory device, the electrical circuitry communicating the determined analyte concentration to the memory device for storage, and
(iii) means for distinguishing an alternative site test from a standard site test;
marking the determined analyte concentration with a marker, the marker being linked to the determined analyte concentration, the marker distinguishing the determined analyte concentration as being from the fluid sample collected from either an alternative test site or a standard test site.

Alternative Process BB

The method of Alternative Process BA wherein the marker is linked to the determined analyte concentration when the fluid sample is collected from the alternative test site.

Alternative Process BC

The method of Alternative Process BB wherein the marker is an AST marker.

Alternative Process BD

The method of Alternative Process BC further comprising the act of flagging the determined analyte concentration when the concentration is determined within a predetermined time period from a prior test.

Alternative Process BE

The method of Alternative Process BA wherein the marker is linked to the determined analyte concentration when the fluid sample is collected from the standard test site.

Alternative Process BF

The method of Alternative Process BA further comprising the act of communicating at least one of the determined analyte concentrations stored in the memory device of the meter to an external device via a communication interface in communication with at least one of the electrical circuitry and the memory device of the meter.

Alternative Process BG

The method of Alternative Process BF wherein the at least one of the determined analyte concentrations is communicated along with a marker linked thereto.

Alternative Process BH

The method of Alternative Process BF wherein the at least one of the determined analyte concentrations is communicated along with a date and time stamp linked thereto.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. An integrated meter for determining a concentration of an analyte in a fluid sample located on a test sensor, the meter comprising:
 a housing;
 a memory device coupled to the housing and adapted to store information;
 a sample collection system coupled to the housing and including a sample collection mechanism and a detection device, the sample collection mechanism being configured to obtain the fluid sample, and the detection device including a sensor connected to the sample collection mechanism and adapted to detect a characteristic of the sample collection mechanism; and
 an electrical circuitry coupled to the housing and adapted to operatively connect to the test sensor and determine the analyte concentration of the fluid sample located on the test sensor, the electrical circuitry being in electronic communication with the memory device, the electrical circuitry being further adapted to communicate the determined analyte concentration to the memory device for storage, the electrical circuitry including a first communication interface adapted to communicate with the sample collection system,
 wherein the sample collection mechanism is adapted to obtain the fluid sample from a first test site or a second test site on a test subject, the sample collection system including a second communication interface, the detection device being adapted to determine, from the characteristic of the sample collection mechanism detected by the sensor, whether the sample collection system is being used to obtain the fluid sample from the first test site or the second test site, the second communication interface being adapted to communicate the determined test site to the first communication interface,
 wherein the memory device is configured to store, in association with the analyte concentration, a marker indicating whether the fluid sample was obtained from the first test site or the second test site.

2. The meter of claim 1, wherein the first communication interface is adapted to communicate information provided by at least one of the electrical circuitry and the memory device to an external device.

3. The meter of claim 2, wherein the first communication interface is adapted to include with the information communicated to the external device at least one determined analyte concentration.

4. The meter of claim 3, wherein the first communication interface is adapted to include with the information communicated to the external device an indication of whether the fluid sample for the determined analyte concentration was obtained from the first test site or the second test site.

5. The meter of claim 3, wherein the first communication interface is adapted to include with the information communicated to the external device a date and time stamp linked to each of the at least one determined analyte concentration.

6. The meter of claim 1, wherein the second communication interface is configured to communicate the determined test site via radio frequency.

7. The meter of claim 1, wherein the second communication interface is configured to communicate the determined test site via infra-red.

8. A sample collection system for obtaining a fluid sample, the sample collection system comprising:
 a sample collection mechanism configured to selectively obtain the fluid sample;
 a detection device with a sensor operatively connected to the sample collection mechanism and adapted to detect a characteristic of the sample collection mechanism, the detection device being adapted to determine, from the detected characteristic, whether the sample collection system is being used to obtain the fluid sample from a first test site or a second test site; and
 a communication interface adapted to communicate wirelessly with a meter, the meter being adapted to determine an analyte concentration from the fluid sample, the communication interface being adapted to wirelessly communicate, from the sensor to the meter, whether the fluid sample was obtained from the first test site or the second test site, the meter including a memory device that is configured to store, in association with the analyte concentration, a marker indicating whether the fluid sample was obtained from the first test site or the second test site.

9. The sample collection system of claim 8, wherein the wireless communication interface is configured to communicate the determined test site wirelessly via radio frequency.

10. The sample collection system of claim 8, wherein the wireless communication interface is configured to communicate the determined test site wirelessly via infra-red.

11. The sample collection system of claim 8, wherein the sample collection mechanism includes a lancing mechanism with an endcap, a lance partially disposed in the endcap, and an adjustment mechanism for the lance, the adjustment mechanism being configured to adjust the depth that the lance extends from a face of the endcap, and wherein the detection device is configured to determine whether the fluid sample is from the first test site or the second test site by the sensor monitoring the adjustment mechanism.

12. The sample collection system of claim 8, wherein the sample collection mechanism includes a lancing mechanism with a lance, and the detection device is configured to determine whether the fluid sample is from the first test site or the second test site by the sensor detecting a distance that the lance extends from the lancing mechanism.

13. The sample collection system of claim 8, wherein the sample collection mechanism includes a lancing mechanism with first and second removable endcaps configured to obtain fluid samples from the first and second test sites, respectively, and the detection device is configured to determine whether the fluid sample is from the first test site or the second test site according to the sensor detecting whether the first removable endcap or the second removable endcap is attached to the lancing mechanism.

14. The sample collection system of claim 8, wherein the meter includes an input device configured to receive a manual entry from a user, the meter being configured to mark the analyte concentration as being from the first test site or the second test site according to the manual entry from the user.

15. A system for determining a concentration of an analyte in a fluid sample located on a test sensor, the system comprising:
   a meter, including:
      a memory device adapted to store information;
      an electrical circuitry adapted to operatively connect to the test sensor and determine the analyte concentration of the fluid sample located on the test sensor, the electrical circuitry being in electronic communication with the memory device, the electrical circuitry being further adapted to communicate the determined analyte concentration to the memory device for storage; and
      a first communication interface; and
   a sample collection system adapted to obtain the fluid sample from a first test site or a second test site on a test subject, the sample collection system including:
      a sample collection mechanism configured to selectively obtain the fluid sample;
      a detection device with a sensor operatively connected to the sample collection mechanism and adapted to detect a characteristic of the sample collection mechanism, the detection device being adapted to determine whether the sample collection system is being used to obtain a fluid sample from the first test site or the second test site; and
      a second communication interface adapted to communicate with the first communication interface of the meter, the second communication interface being configured to communicate, from the detection device to the first communication interface, whether the fluid sample was obtained from the first test site or the second test site,
   wherein the memory device of the meter is configured to store, in association with the analyte concentration, a marker indicating whether the fluid sample was obtained from the first test site or the second test site.

16. The system of claim 15, wherein the second communication interface is configured to communicate the determined test site wirelessly via radio frequency.

17. The system of claim 15, wherein the second communication interface is configured to communicate the determined test site wirelessly via infra-red.

18. The system claim 15, wherein the first communication interface is adapted to communicate information provided by at least one of the electrical circuitry and the memory device to an external device.

19. The system of claim 18, wherein the first communication interface is adapted to include with the information communicated to the external device at least one determined analyte concentration.

20. The system of claim 19, wherein the first communication interface is adapted to include with the information communicated to the external device an indication of whether the fluid sample for the at least one determined analyte concentration was obtained from the first test site or the second test site.

* * * * *